US012651661B2

(12) United States Patent
Jeon et al.

(10) Patent No.: US 12,651,661 B2
(45) Date of Patent: Jun. 9, 2026

(54) METHOD, DEVICE, AND COMPUTER PROGRAM PRODUCT FOR DETERMINING INACTIVE TIME OF DRUG INFUSION CALCULATOR

(71) Applicant: IPV, Seoul (KR)

(72) Inventors: Yongho Jeon, Gwangmyeong-si (KR); Seonhwan Kim, Seongnam-si (KR); Youngjin Jung, Yongin-si (KR)

(73) Assignee: IPV, Seoul (KR)

( * ) Notice: Subject to any disclaimer, the term of this patent is extended or adjusted under 35 U.S.C. 154(b) by 369 days.

(21) Appl. No.: 18/107,074

(22) Filed: Feb. 8, 2023

(65) Prior Publication Data

US 2023/0187048 A1     Jun. 15, 2023

Related U.S. Application Data

(63) Continuation of application No. PCT/KR2021/008629, filed on Jul. 7, 2021.

(30) Foreign Application Priority Data

Aug. 13, 2020     (KR) ........................ 10-2020-0101685

(51) Int. Cl.
*G16H 20/17*          (2018.01)
*A61M 5/168*          (2006.01)
(52) U.S. Cl.
CPC ............ *G16H 20/17* (2018.01); *A61M 5/168* (2013.01)
(58) Field of Classification Search
None
See application file for complete search history.

(56) References Cited

U.S. PATENT DOCUMENTS

| | | | |
|---|---|---|---|
| 2009/0105636 A1 | 4/2009 | Hayter | |
| 2018/0214634 A1 | 8/2018 | Neftel et al. | |
| 2020/0246541 A1 | 8/2020 | Neftel | |
| 2022/0323695 A1 | 10/2022 | Albertini | |

FOREIGN PATENT DOCUMENTS

| | | | |
|---|---|---|---|
| EP | 2335755 A1 | 6/2011 | |
| EP | 2365453 B1 | 4/2020 | |
| JP | 2006034323 A | 2/2006 | |
| JP | 2017-529149 A | 10/2017 | |
| KR | 1020190001962 A | 1/2019 | |
| KR | 102134627 B1 | 7/2020 | |
| KR | 10-2022-0087763 A | 6/2022 | |
| KR | 10-2022-0088703 A | 6/2022 | |
| WO | 2009103492 A1 | 8/2009 | |
| WO | 2010025427 A1 | 3/2010 | |

OTHER PUBLICATIONS

Japanese Office Action for JP 2023-510404 issued on Jan. 30, 2024.
Japanese Notice of Allowance for JP 2023-510404 issued on Aug. 6, 2024.
Omnipod DASH Insulin Management System User Guide; URL: www.myomnipod.com.

*Primary Examiner* — Manuel A Mendez
(74) *Attorney, Agent, or Firm* — Dinsmore & Shohl LLP; Yongsok Choi, Esq.

(57) ABSTRACT

A method and apparatus for determining an inactive time of a medical liquid dose calculator are provided. According to the method, an infusion error of a medical liquid infusion device may be detected, and an inactive time of the medical liquid dose calculator may be determined in response to detection of the infusion error.

6 Claims, 9 Drawing Sheets

METHOD, DEVICE, AND COMPUTER PROGRAM PRODUCT FOR DETERMINING INACTIVE TIME OF DRUG INFUSION CALCULATOR

CROSS-REFERENCE TO RELATED APPLICATIONS

This application is a continuation of International Application No. PCT/KR2021/008629 filed on Jul. 7, 2021, which claims priority to Korean Patent Application No. 10-2020-0101685 filed on Aug. 13, 2020, the entire contents of which are herein incorporated by reference.

TECHNICAL FIELD

The disclosure provides a method, device, and computer program product for determining an inactive time of a medical liquid dose calculator.

BACKGROUND ART

Diabetes mellitus is a metabolic disorder that causes symptoms in which blood glucose levels are out of the normal range due to an insufficient secretion of insulin or a failure in its normal function. Diabetes is a complex disease that can affect each tissue of the human body due to complications such as blindness, renal failure, heart failure, and neuropathy, and the number of diabetic patients is reported to be increasing every year.

In the case of diabetes, it is necessary to measure blood sugar by using a blood glucose meter and control blood sugar through appropriate means such as diet, exercise programs, insulin injection, oral diabetes medicine, and the like.

Recently, when a medical liquid infusion device is discarded due to an abnormal reason, it is not possible to determine the exact amount of bolus actually injected into a user, and thus, a technique for solving this problem is required.

SUMMARY

Technical Problem

The disclosure provides a method, apparatus and computer program product for determining an inactive time of a medical liquid dose calculator. The technical objective to be achieved by the present embodiments is not limited to those described above, and other technical objectives can be inferred from the following embodiments.

Technical Solution to Problem

As a technical means for achieving the above-described technical objective, according to an aspect of the disclosure, there is provided is a method of determining an inactive time of a medical liquid dose calculator, the method including detecting an infusion error of a medical liquid infusion device, and determining an inactive time of the medical liquid dose calculator in response to the detecting of the infusion error.

According to another aspect of the disclosure, there is provided an apparatus for determining an inactive time of a medical liquid dose calculator, the apparatus including a memory storing at least one program, and a processor configured to perform calculations by executing the at least one program, wherein the processor is further configured to detect an infusion error of a medical liquid infusion device, and determine an inactive time of the medical liquid dose calculator in response to detection of the infusion error.

According to another aspect of the disclosure, there is provided a computer program product including a computer-readable recording medium having stored therein a program for executing a method, the method including detecting an infusion error of a medical liquid infusion device, and determining an inactive time of a medical liquid dose calculator in response to the detecting of the infusion error.

Advantageous Effects of Disclosure

According to the means for solving the problem of the disclosure, when a medical liquid infusion device is discarded due to an abnormal reason, by inactivating a medical liquid dose calculator for a certain period of time, the risk of over/under infusion of insulin may be prevented in advance.

DETAILED DESCRIPTION

Figure 1:
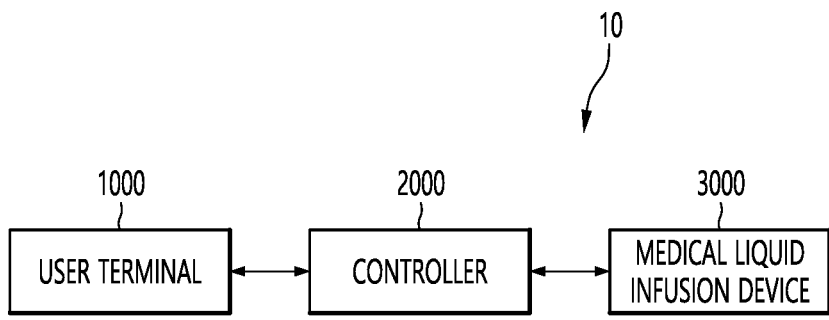
FIG. 1 is a block diagram of an insulin management system including a user terminal, a controller, and a medical liquid infusion device.

A method and apparatus for determining an inactive time of a medical liquid dose calculator may be provided. According to the method of the disclosure, an infusion error of a medical liquid infusion device may be detected, and an inactive time of a medical liquid dose calculator may be determined in response to the detection of the infusion error.

Mode of Disclosure

Hereinafter, embodiments of the disclosure will be described in detail so that those skilled in the art can easily practice the disclosure with reference to the accompanying drawings. However, the disclosure may be embodied in many different forms and is not limited to the embodiments described herein. And in order to clearly explain the disclosure in the drawings, parts irrelevant to the description are omitted, and similar reference numerals are attached to similar parts throughout the specification.

Throughout the specification, when a part is "connected" to another part, it may be construed that the part is "directly connected" but also the part is "electrically connected" to the other part with another element interposed therebetween. In addition, when a part "includes" a component, it does not mean that the part does not include components other than the mentioned component but may include other components provided that there is no indication to the contrary.

Hereinafter, the disclosure will be described in detail with reference to the accompanying drawings.

FIG. 1 is a block diagram of an insulin management system including a user terminal, a controller, and a medical liquid infusion device.

A user terminal 1000 refers to a communication terminal capable of using a web service in a wired or wireless communication environment. For example, the user terminal 1000 may include a smart phone, a tablet personal computer (PC), a PC, a smart TV, a mobile phone, a personal digital assistant (PDA), a laptop computer, a media player, a micro server, a global positioning system (GPS) device, an e-book reader, a terminal for digital broadcasting, a navigation device, a kiosk, an MP3 player, a digital camera, a home appliance, a camera-mounted device, and other mobile or non-mobile computing devices. Also, the user terminal 1000 may include a wearable device having a communication function and a data processing function, such as a watch, glasses, a hair band, and a ring. However, as described above, a terminal equipped with an application capable of internet communication may be used without limitation.

The user terminal 1000 may be connected with a pre-registered controller 2000 in a one-to-one manner. Also, the user terminals 1000 may receive data from the controller 2000 in order to prevent control by an external device. The user terminal 1000 may transmit setting information, for example, system time information to the controller 2000 within a preset range.

The controller 2000 performs a function of transmitting and receiving data to and from a medical liquid infusion device 3000, and may transmit a control signal related to infusion of a medical liquid, such as insulin, to the medical liquid infusion device 3000, and receive, from the medical liquid infusion device 3000, a control signal related to the measurement of a biometric value such as blood glucose.

The controller 2000 may transmit an instruction request to measure a current state of a user, to the medical liquid infusion device 3000, and receive measurement data from the medical liquid infusion device 3000 in response to the instruction request.

While the medical liquid infusion device 3000 performs a function of measuring the user's biometric values such as blood sugar level, blood pressure, heart rate, etc., but also a function of infusing a medical liquid to be infused into the user, such as insulin, glucagon, anesthetic, painkiller, dopamine, growth hormone, and smoking cessation aids.

The medical liquid infusion device 3000 may further include a storage unit that stores a substance to be periodically infused into a user, and may be controlled such that a dose to be infused is infused from the storage unit, according to an infusion signal generated by a controller.

Here, the medical liquid infusion device 3000 may transmit information such as measured values and infusion doses to the controller 2000. Selectively, the medical liquid infusion device 3000 may transmit a device status message, a biometric value measurement message, and a medical liquid infusion message to the controller 2000. For example, the medical liquid infusion device 3000 may transmit, to the controller 2000, a device status message including remaining battery capacity information of the device, whether the device boots successfully, and whether the infusion is successful. Messages delivered to the controller 2000 may be delivered to the user terminal 1000 via the controller 2000. Alternatively, the controller 2000 may transmit improved data obtained by processing received messages, to the user terminal 1000.

The medical liquid infusion device 3000 may also be implemented to communicate only with pre-registered controllers. In addition, in terms of hardware, the medical liquid infusion device 3000 may be classified into a measurement device that performs a function of measuring biometric values such as a user's blood sugar level, blood pressure, and heart rate, and an infusion device that performs a function of infusing a medical liquid such as insulin, glucagon, anesthetic, etc. That is, the measurement device and the infusion device may exist independently of each other. The controller 2000 may be connected to each of the infusion device and the measurement device to generate and provide a control signal for the infusion device based on a measurement value measured using the measurement device.

The user terminal 1000, the controller 2000, and the medical liquid infusion device 3000 may perform communication by using a network. For example, the network may include a Local Area Network (LAN), a Wide Area Network (WAN), a Value Added Network (VAN), a mobile radio communication network, a satellite communication network, and a mutual combination thereof, and refers to a comprehensive data communication network that allows each network constituent entity to communicate smoothly with each other, and may include wired Internet, wireless Internet, and mobile wireless communication networks. In addition, wireless communication may include, for example, wireless LAN (Wi-Fi), Bluetooth, Bluetooth low energy, Zigbee, Wi-Fi Direct (WFD), ultra wideband (UWB), infrared communication (IrDA, infrared Data Association), Near Field Communication (NFC), etc., but are not limited thereto.

Figure 2A:
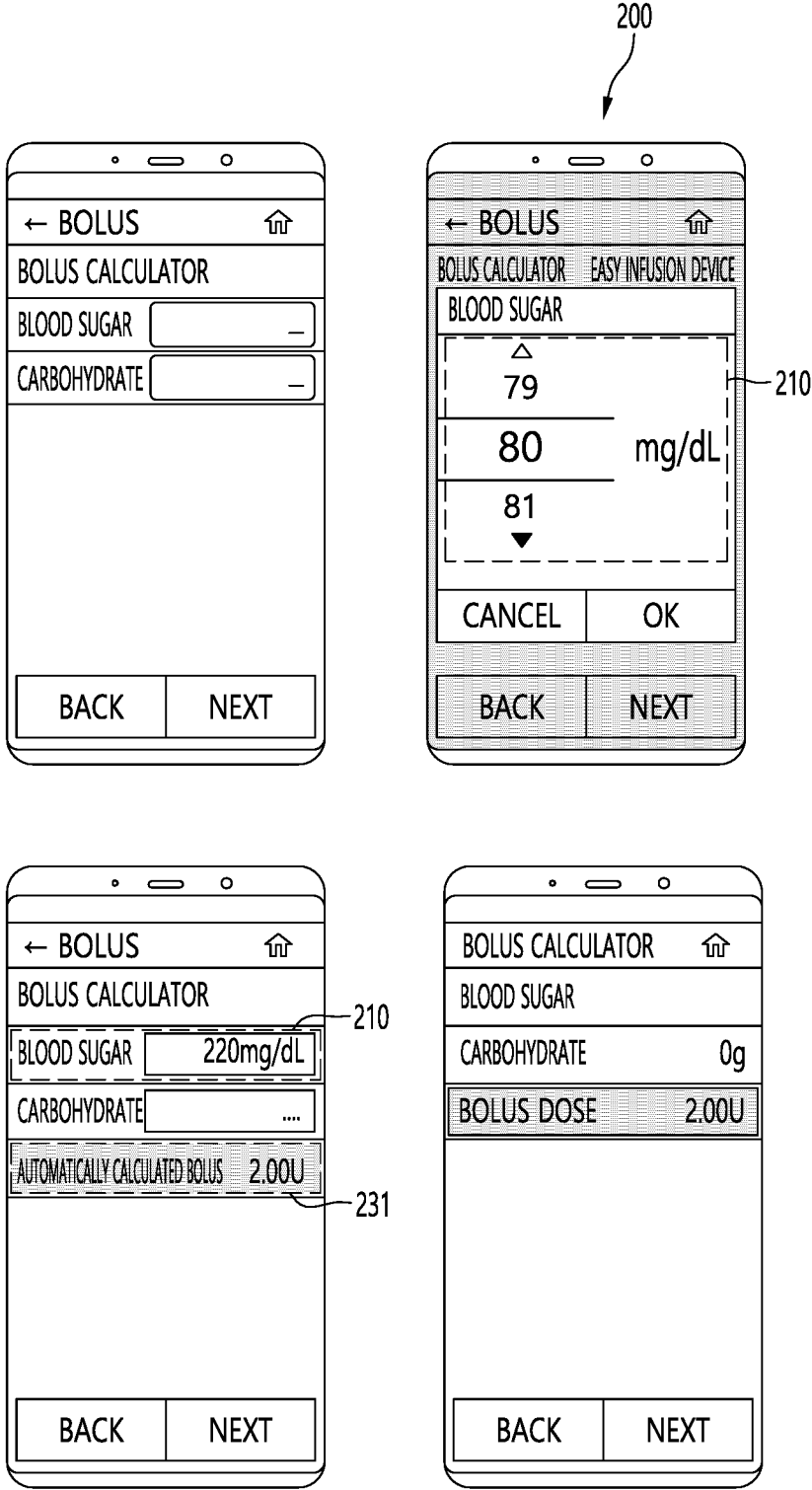
FIGS. 2A to 2B are diagrams for explaining a method of setting a medical liquid dose calculator, according to an embodiment.
Figure 2B:
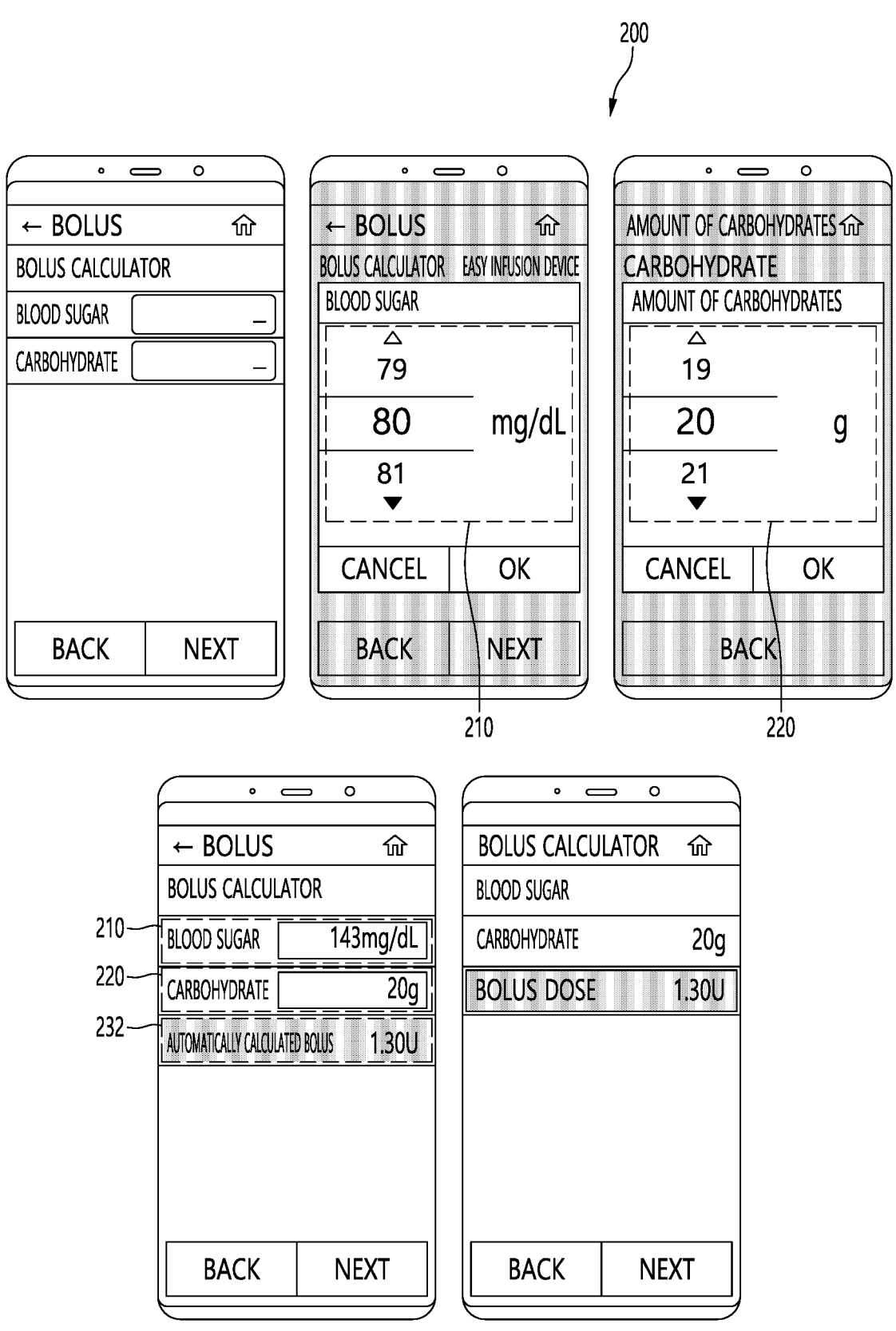

FIGS. 2A to 2B are diagrams for explaining a method of setting a medical liquid dose calculator, according to an embodiment.

A medical liquid dose calculator may be mounted in the user terminal 1000, the controller 2000, or the medical liquid infusion device 3000 of FIG. 1. The medical liquid dose calculator may include a calculator that calculates an amount of insulin to be infused into a user, separately from basic infusion. For example, the medical liquid dose calculator may calculate an amount of insulin needed to bring down blood sugar that rises from food or snacks. In addition, the medical liquid dose calculator may calculate an amount of insulin required to lower high blood sugar to a normal blood sugar range.

As described above, apart from the basal insulin infusion, insulin infused due to food intake or to lower high blood sugar may be referred to as a bolus. The medical liquid infusion calculator may be referred to as a bolus calculator, and the bolus calculator may calculate a bolus dose.

The bolus dose may be determined by various values. For example, the bolus dose may be determined based on a current blood glucose level, a carbohydrate-to-insulin ratio, a calibration coefficient, a target blood glucose level, and the amount of insulin remaining with activation time in the body among a previous bolus dose (Insulin On Board (10B), Bolus on Board, or Active Insulin), a calibration threshold, an amount of activity, type and amount of ingested food, etc.

The calibration coefficient is a value indicating a blood glucose level that 1 unit of bolus insulin can lower. A range of the calibration coefficient is from about 1 mg/dl/U to about 400 mg/dl/U, and may be adjusted by 1 mg/dl/U. The calibration threshold may refer to a highest blood glucose level at which it is determined that insulin infusion is required to control blood sugar.

The bolus calculator may calculate a bolus dose based on the user's individual bolus profile set value, current blood sugar level, amount of ingested carbohydrates, and remaining body insulin level (10B).

In detail, the bolus profile set value may be determined by a target blood glucose level, a carbohydrate-to-insulin ratio, a calibration coefficient, and insulin duration. The current blood glucose value refers to a blood glucose value measured within 10 minutes.

Referring to FIG. 2A, the user may input a current blood glucose value 210 into the medical liquid dose calculator. The user may omit the input of the amount of ingested carbohydrates. The user may input the current blood glucose value 210 in units of mg/dl. For example, the user may input 220 mg/dl as the current blood glucose value 210. The medical liquid dose calculator may calculate 2.00 U as a bolus dose 231 based on the current blood glucose value 210. A unit that may be input as the current blood glucose value 210 may be mmol/l, but is not limited to the above unit example.

Referring to FIG. 2B, the user may input the current blood glucose value 210 and an amount of ingested carbohydrates 220 into the medical liquid dose calculator. The user may input the current blood glucose value 210 in units of mg/dl and the amount of ingested carbohydrates 220 in units of g. For example, the user may input 220 mg/dl as the current blood glucose value 210 and input 20 g as the amount of ingested carbohydrate 220. The medical liquid dose calculator may calculate 1.30 U as the bolus dose 232 based on the current blood glucose value 210 and the amount of ingested carbohydrates 220.

Figure 3:
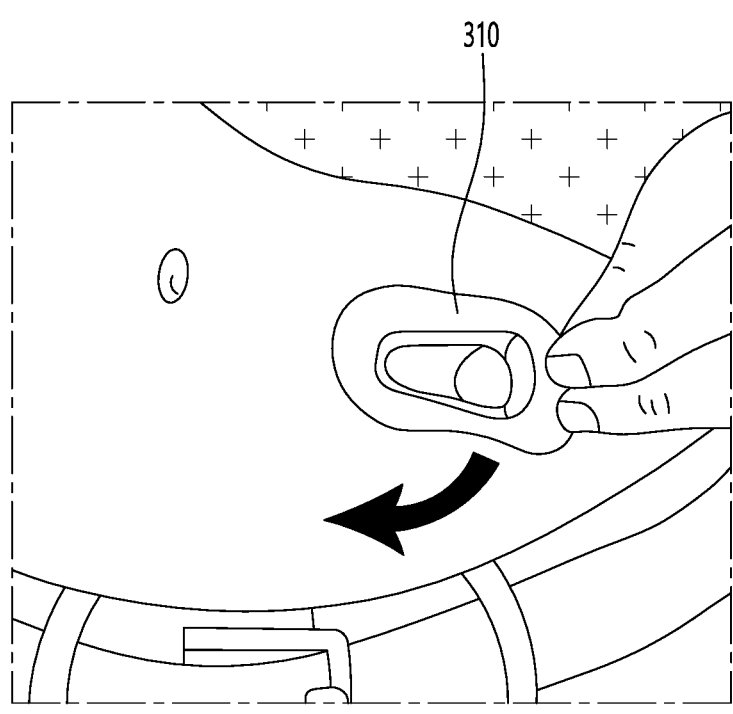
FIG. 3 is a diagram for explaining an example of use and disposal situations of a medical liquid infusion device according to an embodiment.

FIG. 3 is a diagram for explaining an example of use and disposal situations of a medical liquid infusion device according to an embodiment.

While being attached to the body of a user, a medical liquid infusion device 310 may infuse a medical liquid into the user. A certain amount of insulin is stored in a storage unit of the medical liquid infusion device 310.

In an embodiment, a medical liquid dose calculator may be mounted in a controller (not shown). The medical liquid infusion device 310 may transmit or receive data to or from the controller (not shown). The controller (not shown) may transmit bolus dose data calculated by the medical liquid dose calculator, to the medical liquid infusion device 310, and the medical liquid infusion device 310 may infuse insulin stored in the storage unit, to the user, based on the bolus dose.

In another embodiment, the medical liquid dose calculator may be mounted in the medical liquid infusion device 310. The medical liquid infusion device 310 may infuse the insulin stored in the storage unit into the user based on the bolus dose calculated by the medical liquid dose calculator.

The medical liquid infusion device 310 may be discarded for various reasons. For example, when the insulin stored in the storage unit is exhausted, or the use period of the medical liquid infusion device 310 expires, or an insulin infusion error is detected, the medical liquid infusion device 310 may be discarded.

In detail, when the insulin stored in the storage unit is less than a preset threshold value, the medical liquid infusion device 310 may be discarded. Also, when a preset period of time has elapsed after the operation of the medical liquid infusion device 310, the medical liquid infusion device 310 may be discarded.

In addition, the medical liquid infusion device 310 may detect an infusion error in response to the occurrence of occlusion of an inlet of the medical liquid infusion device 310. An infusion error may be detected in response to a communication error occurring between the controller (not shown) and the medical liquid infusion device 310. A detailed description of a situation in which an infusion error occurs will be described later with reference to FIGS. 5 and 6.

Alternatively, when the user needs to dispose of the medical liquid infusion device 310, the medical liquid infusion device 310 may be discarded and detached from the body.

As described above with reference to FIGS. 2A and 2B, in order to calculate a bolus dose by the medical liquid dose calculator, the user needs to know the exact bolus amount that is actually infused. The medical liquid infusion device 310 may be discarded for various reasons. When the medical liquid infusion device 310 is discarded for normal reasons, the user may be able to identify the exact amount of actually infused bolus, whereas when the medical liquid infusion device 310 is discarded for an abnormal reason, the exact amount of actually infused bolus into the user may not be determined. Accordingly, when the medical liquid infusion device 310 is discarded due to an abnormal reason, the risk of over/under infusion of insulin may be prevented in advance by inactivating the medical liquid dose calculator for a certain period of time.

An inactive time of the medical liquid dose calculator may be determined according to the reason for discarding the medical liquid infusion device 310. When the medical liquid infusion device 310 is discarded for a normal reason, the medical liquid dose calculator may operate without a separate inactive time. For example, when the insulin stored in the storage unit is exhausted or the medical liquid infusion device 310 is discarded due to expiration of the use period of the medical liquid infusion device 310, the medical liquid dose calculator may operate without a separate inactive time.

When the medical liquid infusion device 310 is discarded due to an abnormal reason, the medical liquid dose calculator may operate after a certain inactive time. In detail, when an infusion error is detected in the medical liquid infusion device 310, the medical liquid dose calculator may operate after a certain inactive time. For example, when occlusion of an inlet of the medical liquid infusion device 310 has occurred or a communication error between a controller (not shown) and the medical liquid infusion device 310 has occurred, the medical liquid dose calculator may operate after a certain inactive time.

Figure 4:
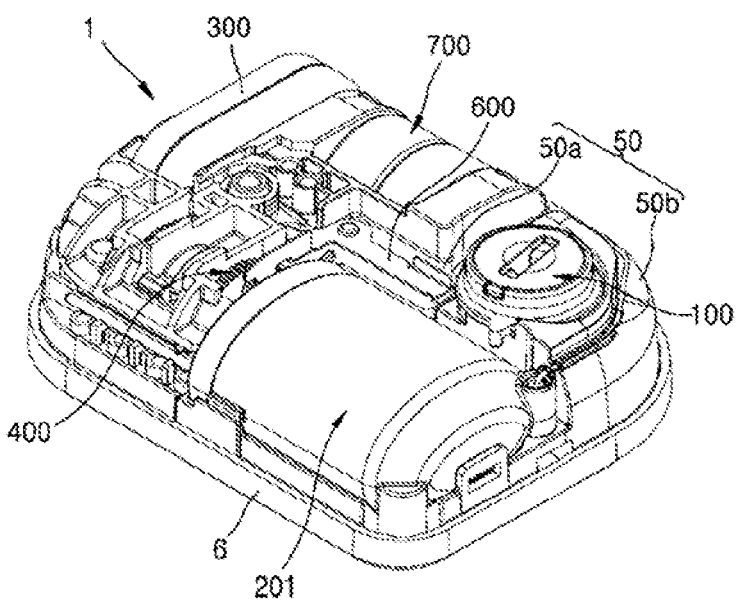
FIG. 4 is a diagram for explaining a case in which occlusion of an inlet of a medical liquid infusion device according to an embodiment has occurred blocked.
Figure 4:
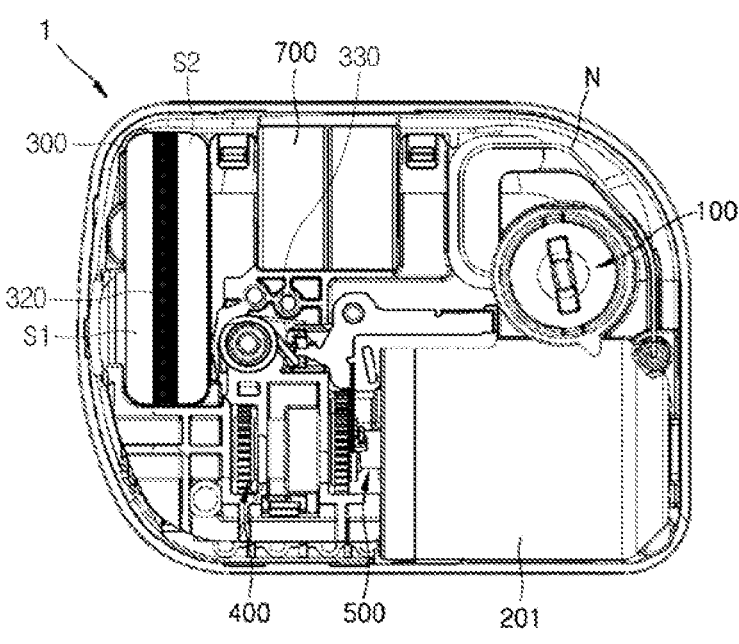

FIG. 4 is a diagram for explaining a case in which occlusion of an inlet of a medical liquid infusion device according to an embodiment has occurred.

Referring to FIG. 4, a medical liquid infusion device 1 may include a housing 5 covering the outside thereof, and an attachment portion 6 attached to the skin of a user. In the medical liquid infusion device 1, a plurality of parts are arranged in an inner space between the housing 5 and the attachment portion 6.

The medical liquid infusion device 1 may include a base body 50, a needle assembly 100, a storage unit 201, a driver 300, a driving unit 400, a clutch unit 500, a trigger member 600, and a battery 700.

The base body 50 forms a basic frame of the housing 5 and is mounted in an inner space of the housing 5. The base body 50 may be provided in plurality. In an embodiment, a first body 50a covering upper portions of internal components and a second body 50b covering lower portions of the internal components may be provided. The first body 50a and the second body 50b may be assembled to fix the internal components of the medical liquid infusion device 1 at preset positions. In another embodiment, the base body 50 may be formed as a single, integral frame.

The storage unit 201 is mounted on the base body 50 and fluidly connected to the needle assembly 100. Inside the storage unit 201, a plunger (not shown) may linearly move to discharge a medical liquid through a needle N.

The driver 300 may generate a driving force and transmit the driving force to the driving unit 400. The driving force transmitted by the driving unit 400 may linearly move a plunger (not shown) inside the storage unit 201 to discharge the medical liquid.

As the driver 300, all types of pumps having a medical liquid suction power and a medical liquid discharging power by electricity may be used. For example, all types of pumps such as a mechanical displacement type micropump and an electromagnetic motion type micropump may be used. The mechanical displacement type micropump is a pump that uses the movement of solids or fluids such as gears or diaphragms to create a pressure difference so as to induce a fluid flow, and examples thereof include diaphragm displacement pumps, fluid displacement pumps, and rotary pumps. The electromagnetic motion type micropump is a pump that uses energy in the form of electricity or magnetism directly to move a fluid, and examples thereof include an electrohydrodynamic pump (EHD), an electroosmotic pump, a magnetohydrodynamic pump, and an electro wetting pump.

When the driving unit 400 is engaged to the driver 300 by the clutch unit 500, the driver 300 rotates a driving wheel of the driving unit 400, and the rotation of the driving wheel may make a rod to linearly move and cause a plunger (not shown) to move inside the storage unit 201.

The driver 300 may include a membrane 320 disposed inside the cover 310. The membrane 320 may partition an inner space of the driver 300 into a first space S1 and a second space S2. The driver 300 may linearly move a driving shaft 330 by a change in volumes of the first space S1 and the second space S2.

On the other hand, in a process of infusing a medical liquid in the storage unit 201, into a patient through the needle N of the needle assembly 100, the inlet, which is a passage through which the medical liquid is infused into the patient, may be blocked due to various foreign substances. The inlet may include an inner passage of the needle N or a medical liquid transfer passage connecting the needle N to the storage unit 201, but is not limited thereto. When the inlet is blocked due to various foreign substances, a necessary amount of medical liquid may not be infused into the patient. Even worse, the medical liquid may not be infused into the patient at all.

In an embodiment, the medical liquid infusion device 1 may determine whether or not the inlet is blocked, based on a driving time of the driver 300. For example, when the driving time of the driver 300 exceeds a threshold value, it may be determined that the inlet is blocked.

According to various embodiments of the disclosure, the medical liquid infusion device 1 may determine whether an occlusion has occurred in a medical liquid discharge path due to foreign substances or the like, and notify the user of the occlusion and that a problem has occurred in the medical liquid infusion device 1.

When a control unit of the medical liquid infusion device 1 determines that occlusion has occurred in the inlet of the medical liquid infusion device 1, the control unit may transmit, to a notification unit, status information indicating that the occlusion has occurred. The notification unit may receive the status information from the control unit and express that the occlusion has occurred, to the outside. For example, the notification unit may output a sound indicating that occlusion has occurred or transmit, to an external device, information indicating that occlusion has occurred.

The user of the medical liquid infusion device 1 may discard the medical liquid infusion device 1 after receiving notification that occlusion in the inlet of the medical liquid infusion device 1 has occurred, through the notification unit. Discarding of the medical liquid infusion device 510 due to occlusion of the inlet of the medical liquid infusion device 1 corresponds to discarding due to abnormal reasons.

In an embodiment, the medical liquid infusion device 1 may transmit, to a controller (not shown), status information indicating that occlusion of the inlet has occurred. The controller (not shown) may detect an infusion error in response to receiving the status information indicating that occlusion of the inlet has occurred, and inactivate a medical liquid dose calculator mounted in the controller (not shown) for a certain period of time. In another embodiment, the medical liquid dose calculator may be mounted on the medical liquid infusion device 1.

Figure 5:
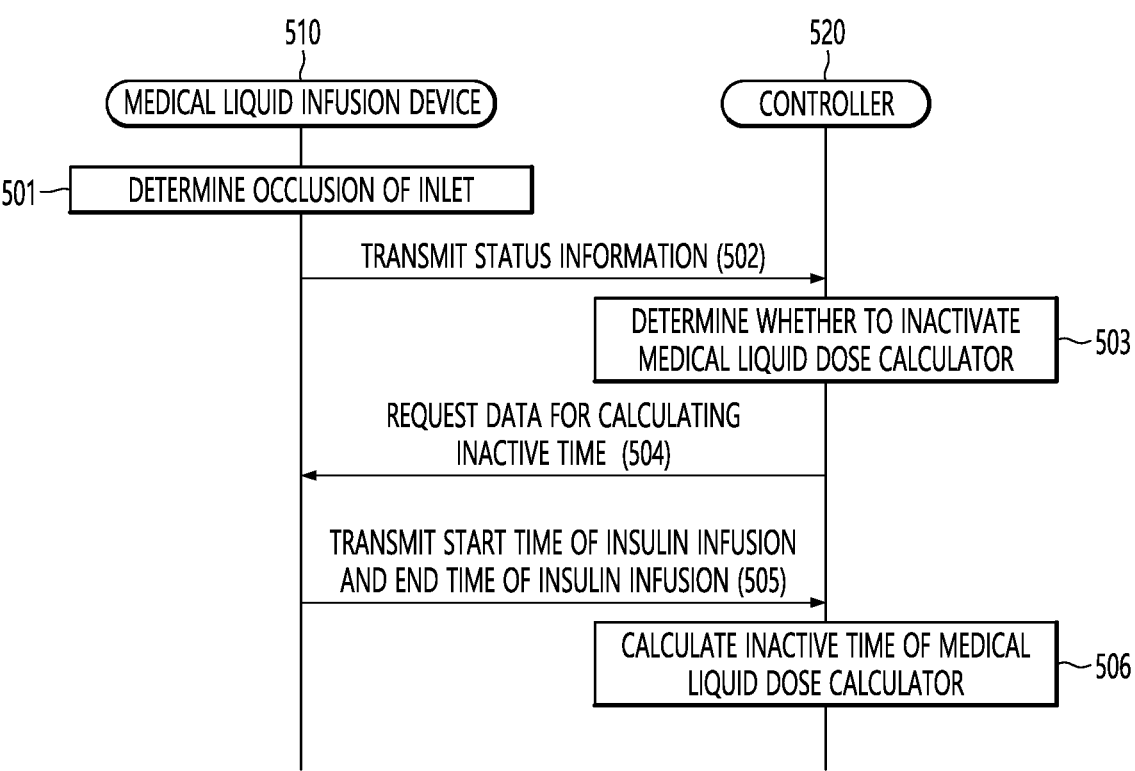
FIG. 5 is a flowchart of a method of calculating an inactive time of a medical liquid dose calculator when occlusion of an inlet of a medical liquid infusion device has occurred, according to an embodiment.

FIG. 5 is a flowchart of a method of calculating an inactive time of a medical liquid dose calculator when occlusion of an inlet of a medical liquid infusion device has occurred, according to an embodiment.

Referring to FIG. 5, a medical liquid infusion device 510 and a controller 520 may communicate with each other. The controller 520 may include a component included in a user terminal such as a smart phone or a PC, or may include a component independent of the user terminal. While the controller 520 communicating with the medical liquid infusion device 510 is illustrated in FIG. 5, the controller 520 may be a component included in the medical liquid infusion device 510. Hereinafter, it is assumed that the medical liquid infusion device 510 and the controller 520 perform communication using a network.

The medical liquid dose calculator may be mounted in the controller 520. The medical liquid dose calculator may include a calculator that calculates an amount of insulin to be infused into a user, separately from basic infusion. For example, the medical liquid dose calculator may calculate an amount of insulin needed to bring down blood sugar that rises from food or snacks. In addition, the medical liquid dose calculator may calculate an amount of insulin required to lower high blood sugar to a normal blood sugar range.

While being attached to the body of a user, the medical liquid infusion device 510 may infuse a medical liquid into the user. In addition, the medical liquid infusion device 510 may be discarded for various reasons. In detail, the medical liquid infusion device 510 may be discarded due to normal or abnormal reasons. When the medical liquid infusion device 510 is discarded for a normal reason, the exact amount of bolus that is actually infused into the user may be identified, and thus, the medical liquid dose calculator may operate without inactive time. On the other hand, when the medical liquid infusion device 510 is discarded due to an abnormal reason, it is difficult to determine the exact amount of bolus actually infused into the user, and thus, the medical liquid dose calculator needs to be inactivated for a certain period of time.

In operation 501, the medical liquid infusion device 510 may determine that occlusion in the inlet has occurred. For example, the medical liquid infusion device 510 may determine whether or not occlusion in the inlet has occurred, based on a driving time of a driver that drives a pump. Alternatively, the medical liquid infusion device 510 may determine that occlusion in the inlet has occurred, in response to detection of a decrease in a current flowing through the pump. The occlusion of the inlet is an infusion error and corresponds to an abnormal reason among the reasons for discarding the medical liquid infusion device 510.

In operation 502, the medical liquid infusion device 510 may transmit, to the controller 520, status information indicating that occlusion in the inlet has occurred.

In operation 503, the controller 520 may determine whether to inactivate the medical liquid dose calculator. In detail, the controller 520 may determine to inactivate the medical liquid dose calculator in response to receiving status information indicating that occlusion in the inlet has occurred.

In operation 504, the controller 520 may request data for calculating the inactive time from the medical liquid infusion device 510.

In operation 505, the medical liquid infusion device 510 may transmit information about a start time of insulin infusion and an end time of insulin infusion, to the controller 520.

In operation 506, the controller 520 may calculate the inactive time of the medical liquid dose calculator. The controller 520 may receive information about the start time of insulin infusion and the end time of insulin infusion, and calculate a reference time for insulin infusion based on the star time of insulin infusion and the end time of insulin infusion. In addition, the controller 520 may acquire a current time and preset insulin duration.

In an embodiment, the controller 520 may determine an inactive time of the medical liquid dose calculator, based on the current time, the preset insulin duration, and the reference time for insulin infusion.

For example, when the start time of insulin infusion is 13:00 PM and the end time of insulin infusion is 14:00 PM, the controller 520 may calculate an average value of the start time of insulin infusion and the end time of insulin infusion as the reference time for insulin infusion. That is, the reference time for insulin infusion is 13:30 PM.

The controller 520 may determine the inactive time by adding the insulin duration to the reference time for insulin infusion and subtracting the current time from the reference time for insulin infusion. For example, when the reference time for insulin infusion is 13:30 PM, the insulin duration is 5 hours, and the current time is 15:00 PM, the controller 520 may set the inactive time of the medical liquid dose calculator to 3 hours and 30 minutes. That is, the medical liquid dose calculator is inactivated until 18:30 PM, which is 3 hours and 30 minutes from the current time (15:00 PM).

Meanwhile, referring to operations 504 to 505 of FIG. 5, the controller 520 receiving information about the start time of insulin infusion and the end time of insulin infusion from the medical liquid infusion device 510 is described. However, in another embodiment, information about the start time and the end time of insulin infusion may be information stored in the controller 520. In this case, the controller 520 may calculate the reference time for insulin infusion based on the stored start time of insulin infusion and the stored end time of insulin infusion, without requesting additional information, and may also calculate an inactive time of the medical liquid dose calculator.

Figure 6:
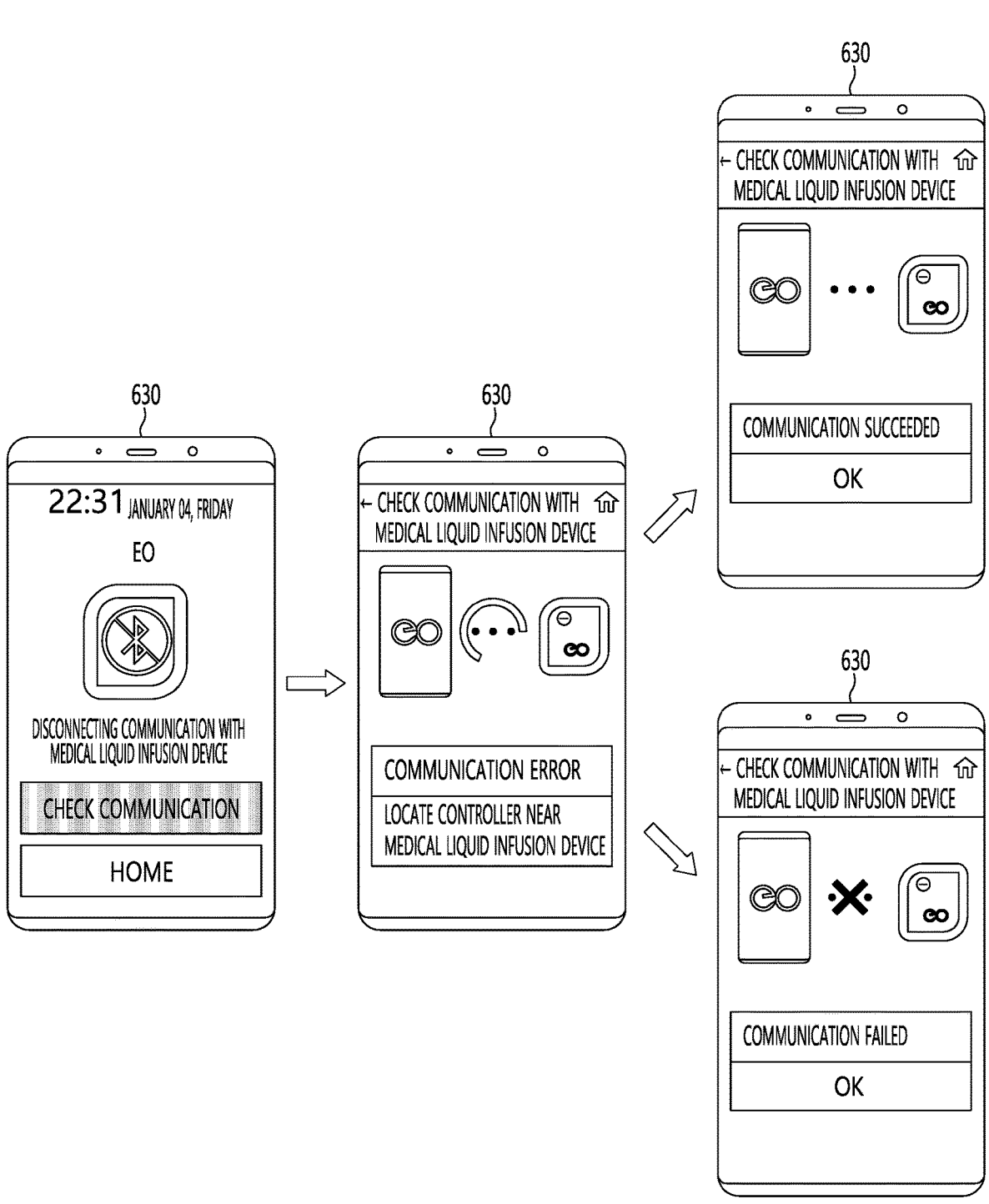
FIG. 6 is a diagram for explaining a case where a communication error occurs in a medical liquid infusion device according to an embodiment.

FIG. 6 is a diagram for explaining a case where a communication error occurs in a medical liquid infusion device, according to an embodiment.

A controller 610 and a medical liquid infusion device 620 may perform communication by using a network. For example, the network may include a LAN, a WAN, a VAN, a mobile radio communication network, a satellite communication network, and a mutual combination thereof, and refers to a comprehensive data communication network that allows each network constituent entity to communicate smoothly with each other, and may include wired Internet, wireless Internet, and mobile wireless communication networks. In addition, wireless communication may include, for example, wireless LAN (Wi-Fi), Bluetooth, Bluetooth low energy, Zigbee, WFD, UWB, infrared communication (IrDA, infrared Data Association), NFC, etc., but are not limited thereto.

A communication state between the controller 610 and the medical liquid infusion device 620 may be displayed through a user terminal 630. This is merely an example, and a communication state between the controller 610 and the medical liquid infusion device 620 may also be displayed through a display of the controller 610 or the medical liquid infusion device 620.

When a communication error occurs between the controller 610 and the medical liquid infusion device 620, the medical liquid infusion device 620 may be discarded. Discarding of the medical liquid infusion device 620 due to a communication error between the controller 610 and the medical liquid infusion device 620 corresponds to discarding due to abnormal reasons.

In an embodiment, the controller 610 may detect an infusion error in response to the occurrence of a communication error, and inactivate a medical liquid dose calculator mounted in the controller 610 for a certain period of time. In another embodiment, the medical liquid dose calculator may be mounted on the medical liquid infusion device 620.

Figure 7:
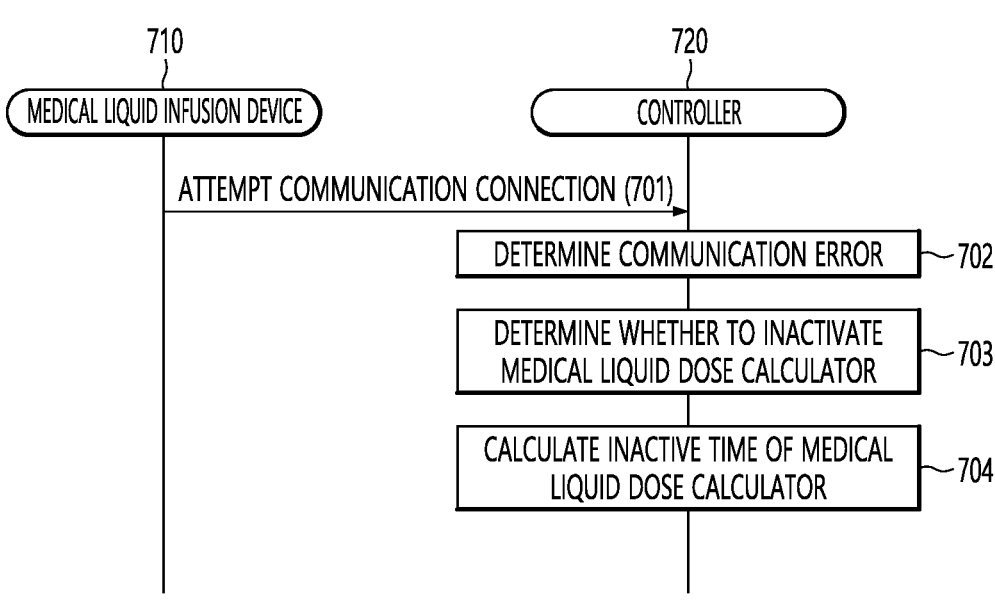
FIG. 7 is a flowchart of a method of calculating an inactive time of a medical liquid dose calculator when a communication error has occurred in a medical liquid infusion device, according to an embodiment.

FIG. 7 is a flowchart of a method of calculating an inactive time of a medical liquid dose calculator when a communication error occurs in a medical liquid infusion device, according to an embodiment.

Referring to FIG. 7, a medical liquid infusion device 710 and a controller 720 may communicate with each other. Descriptions of the medical liquid infusion device 710 and the controller 720 correspond to those provided with reference to FIG. 5, and thus will be omitted here.

While being attached to the body of a user, the medical liquid infusion device 710 may infuse a medical liquid into the user. In addition, the medical liquid infusion device 710 may be discarded for various reasons. In detail, the medical liquid infusion device 710 may be discarded due to normal or abnormal reasons. When the medical liquid infusion device 710 is discarded for a normal reason, the exact amount of bolus that is actually infused into the user may be identified, and thus, and the medical liquid dose calculator may operate without inactive time. On the other hand, when the medical liquid infusion device 710 is discarded due to an abnormal reason, it is difficult to determine the exact amount of bolus actually infused into the user, and thus, the medical liquid dose calculator needs to be inactivated for a certain period of time.

In operation 701, the medical liquid infusion device 710 and the controller 720 may attempt a communication connection with each other.

In operation 702, the controller 720 may determine that a communication error has occurred, when communication with the medical liquid infusion device 710 fails. In detail, the controller 720 may continuously attempt a communication connection with the medical liquid infusion device 710, and as a result, if the communication connection fails a certain number of times or more, the controller 720 may determine that a communication error has occurred.

In operation 703, the controller 520 may determine whether to inactivate the medical liquid dose calculator. In detail, the controller 720 may determine to inactivate the medical liquid dose calculator in response to the occurred communication error.

In operation 704, the controller 720 may calculate an inactive time of the medical liquid dose calculator. In detail, the controller 720 may acquire a current time and preset insulin duration. In addition, the controller 720 may determine, as a communication error occurrence time, a time when it is determined that a communication error occurs in operation 702.

In an embodiment, the controller 720 may determine the inactive time of the medical liquid dose calculator, based on the current time, the preset insulin duration, and the communication error occurrence time.

For example, when the communication error occurrence time is 14:00 PM, the insulin duration is 5 hours, and the current time is 15:00 PM, the controller 720 may set the inactive time of the medical liquid dose calculator to 4 hours. That is, the medical liquid dose calculator is inactivated until 19:00 PM, which is 4 hours from the current time (15:00 PM).

Figure 8:
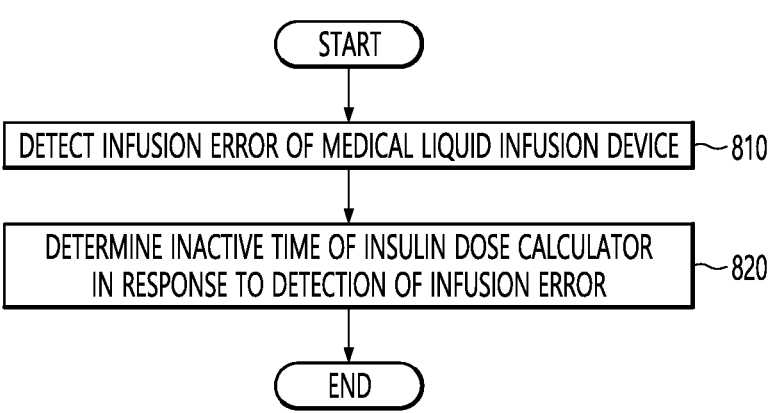
FIG. 8 is a flowchart of a method of determining an inactive time of a medical liquid dose calculator, according to an embodiment.

FIG. 8 is a flowchart of a method of determining an inactive time of a medical liquid dose calculator, according to an embodiment.

In an embodiment, the medical liquid dose calculator may be mounted in a controller. A medical liquid infusion device may transmit or receive data to or from the controller. The controller may transmit bolus dose data calculated by the medical liquid dose calculator, to the medical liquid infusion device, and the medical liquid infusion device may infuse insulin stored in a storage unit, to the user based on the bolus dose. The controller may include a component included in a user terminal such as a smart phone or a PC, or may include a component independent of the user terminal.

In another embodiment, the medical liquid dose calculator may be mounted in the medical liquid infusion device. The medical liquid infusion device may infuse insulin stored in the storage unit, into the user, based on the bolus dose calculated by the medical liquid dose calculator.

Hereinafter, it is assumed that the medical liquid dose calculator is mounted in the controller.

Referring to FIG. 8, in operation 810, the controller may detect an infusion error of the medical liquid infusion device.

In an embodiment, the controller may detect an infusion error in response to occlusion of an inlet of the medical liquid infusion device.

In another embodiment, the controller may detect an infusion error in response to a communication error with respect to the medical liquid infusion device.

In operation 820, the controller may determine an inactive time of the medical liquid dose calculator in response to detection of the infusion error.

When the controller detects an infusion error due to occlusion of the medical liquid infusion device, the controller may calculate a reference time for insulin infusion based on a start time of insulin infusion and an end time of insulin infusion. In addition, the controller may determine an inactive time based on a current time, preset insulin duration, and the reference time for insulin infusion.

When the controller detects an infusion error due to a communication error with respect to the medical liquid infusion device, the controller may obtain a communication error occurrence time when the communication error occurred. In addition, the controller may determine the inactive time based on the current time, the preset insulin duration, and the communication error occurrence time.

Various embodiments of the disclosure may be implemented as software (e.g., a program) including one or more instructions stored in a machine-readable storage medium. For example, a processor of a machine device may call at least one instruction among one or more stored instructions from a storage medium and execute the same. This enables the machine to be operated to perform at least one function according to the at least one instruction invoked. The one or more instructions may include code generated by a compiler or code executable by an interpreter. The machine-readable storage medium may be provided in the form of a non-transitory storage medium. Here, 'non-transitory' only means that the storage medium is a tangible device and does not contain signals (e.g., electromagnetic waves), and this term does not distinguish between a case where data is stored semi-permanently in a storage medium and a case where data is temporarily stored.

According to an embodiment, the method according to various embodiments of the disclosure may be included and provided in a computer program product. Computer program products may be traded between sellers and buyers as commodities. A computer program product is distributed in the form of a machine-readable storage medium (e.g., compact disc read only memory (CD-ROM)), or through an application store (e.g., Play Store™) or between two user devices directly or online (e.g., downloaded or uploaded). In the case of online distribution, at least part of a computer program product may be temporarily stored or temporarily created in a machine-readable storage medium such as a server of a manufacturer, an application store server, or a memory of a relay server.

Also, in this specification, a "unit" may refer to a hardware component such as a processor or a circuit, and/or a software component executed by the hardware component such as a processor.

The scope of the present embodiments is indicated by the appended claims rather than the detailed description above, and should be construed as including all changes or modifications derived from the meaning and scope of the claims and equivalent concepts thereof.

What is claimed is:

1. A method of determining an inactive time of a medical liquid dose calculator, the method comprising:

detecting an infusion error of a medical liquid infusion device in response to occurrence of a communication error with the medical liquid infusion device; and determining an inactive time of the medical liquid dose calculator in response to detection of the infusion error, wherein the determining comprises:

obtaining a communication error occurrence time when the communication error occurred; and determining the inactive time based on a current time, a preset insulin duration, and the communication error occurrence time.

2. The method of claim 1, wherein the detecting comprises detecting an infusion error of the medical liquid infusion device in response to occurrence of occlusion of an inlet of a medical liquid infusion device, wherein the determining comprises:

calculating an insulin infusion reference time based on an insulin infusion start time and an insulin infusion end time; and determining the inactive time based on a current time, a preset insulin duration, and the insulin infusion reference time.

3. An apparatus for determining an inactive time of a medical liquid dose calculator, the apparatus comprising:

a memory in which at least one program is stored; and a processor configured to perform operations by executing the at least one program, wherein the processor is further configured to detect an infusion error of a medical liquid infusion device in response to occurrence of a communication error with the medical liquid infusion device, and determine an inactive time of the medical liquid dose calculator in response to detection of the infusion error, and the processor is further configured to obtain a communication error occurrence time when the communication error occurred, and determine the inactive time based on a current time, a preset insulin duration, and the communication error occurrence time.

4. The apparatus of claim 3, wherein the processor is further configured to detect an infusion error of a medical liquid infusion device in response to occurrence of occlusion of an inlet of the medical liquid infusion device, and the processor is further configured to calculate an insulin infusion reference time based on an insulin infusion start time and an insulin infusion end time, and determine the inactive time based on a current time, a preset insulin duration, and the insulin infusion reference time.

5. A computer program product including a computer-readable recording medium having stored therein a program for executing a method, the method comprising:

detecting an infusion error of a medical liquid infusion device in response to occurrence of a communication error with the medical liquid infusion device; and determining an inactive time of a medical liquid dose calculator in response to detection of the infusion error, wherein the determining comprises:

obtaining a communication error occurrence time when the communication error occurred; and determining the inactive time based on a current time, a preset insulin duration, and the communication error occurrence time.

6. The computer program product of claim 5, wherein the detecting comprises detecting an infusion error of the medical liquid infusion device in response to occurrence of occlusion of an inlet of a medical liquid infusion device, wherein the determining comprises:

calculating an insulin infusion reference time based on an insulin infusion start time and an insulin infusion end time; and determining the inactive time based on a current time, a preset insulin duration, and the insulin infusion reference time.

* * * * *